United States Patent [19]

Nimberg et al.

[11] Patent Number: 4,816,437

[45] Date of Patent: Mar. 28, 1989

[54] METHODS FOR INDUCING GENERAL AND LOCALIZED BONE APPOSITION IN-VIVO

[75] Inventors: Richard B. Nimberg, Sharon; Craig Colclasure, Watertown; Weldon S. Lloyd, Sharon, all of Mass.

[73] Assignee: Trustees of Boston University, Boston, Mass.

[21] Appl. No.: 56,023

[22] Filed: Jun. 1, 1987

[51] Int. Cl.$^4$ .......................... C07C 8/00; A61K 37/02
[52] U.S. Cl. ........................................ 514/8; 530/395; 530/840
[58] Field of Search ...................... 514/8; 530/395, 840

[56] References Cited
PUBLICATIONS

Lewis et al., "Effect of Human $\alpha_2$HS Glycoprotein on Mouse Macrophage Function", *Immunology*, 1980, 39:317.
Gejyo et al., "Purification and Characterization of the Two Forms of Human Plasma $\alpha_2$HS–Glycoprotein", *Biochim. Biophys. Acta*, 671, (1981), 78–84.

*Primary Examiner*—John Kight
*Assistant Examiner*—Nathan M. Nutter
*Attorney, Agent, or Firm*—David Prashker

[57] ABSTRACT

The present invention provides unique methodologies for inducing new bone apposition in-vivo generally or at a localized site and for therapeutically treating a subject afflicted with a pathological disorder of bone which is characterized by a deficiency of calcium ions in the bone matrix. The methodology for treating generalized defective skeletile mineralization comprises administering sufficient quantities of $\alpha_2$HS-glycoprotein to the subject such that the concentration of this naturally occurring plasma protein is not substantially less than about 600 micrograms per milliliter of serum in-vivo. Alternatively, the method for treatment of localized defective skeletile mineralization comprises administration of a therapeutic admixture containing about 300 mircograms of $\alpha_2$HS-glycoprotein per gram of filler material to the site of skeletal defect.

5 Claims, 1 Drawing Sheet

METHODS FOR INDUCING GENERAL AND LOCALIZED BONE APPOSITION IN-VIVO

FIELD OF THE INVENTION

The present invention is concerned generally with the regulation of bone formation and is particularly directed to methods for inducing bone apposition in-vivo; methods for enhancing healing of bone fractures; and methods for therapeutically treating pathological diseases and disorders of bone which are characterized by a deficiency of calcium in the bone matrix.

BACKGROUND OF THE INVENTION

The formation of bone and the regulation of bone formation has been an area of intense scientific interest and investigation for over twenty years. In part, such interest stems from a desire to therapeutically treat pathological disorders and diseases of bone such as those clinical conditions identified as Paget's disease, osteogenesis imperfecta, renal osteodystrophy, osteomalacias, osteopetrosis, and osteoporosis [Quelch et al., *Calcif. Tissue Int.* 36:545–549 (1984)]. Other investigators are primarily concerned with those alterations and changes of human bone which occur with increasing age, such changes being deemed normal although often debilitating to the individual [Dickson and Bagga, *Conn. Tissue Res.* 14:77–85 (1985)]. Regardless of the particular motive, it has become increasingly clear that the formation of bone and the regulation of bone formation must be viewed and understood at three individual levels: the tissue level; the cellular level; and the molecular matrix level [Raisz and Kream, *N.E.J. Med.* 309:29–35 and 83–89 (1983)]. At the tissue level, the concept of coupling of osteoclastic resorption and osteoblastic formation as bone remodeling units has become the central focus and controlling principle of bone metabolism [Harris and Heaney, *N. Engl. J. Med.* 280:253 (1969); Baylink and Liu, *J. Periodontol.* 50:43 (1979); Farley and Baylink, *Trans. Assoc. Am. Physc.* 94:80 (1981)]. In the adult skeleton, bone remodeling involves a coupled sequence of resorption followed by new bone formation which occurs at different sites to produce changes in size or shape and to maintain the mechanical strength of bone. This process is particularly important in the skeletal response to changes in mechanical stress and are, presumably, regulated locally rather than by systemic hormones. Because of these coupled processes, the absolute rates of bone resorption and formation in the skeleton are large relative to the net change in skeletal mass during normal aging. The overall effect, nevertheless, is that net bone mass increases during the first two decades of life and decreases after the third or fourth decade.

The cellular level of bone formation requires an understanding of the origin and fate of osteoblasts [Owen, M., *Calcif. Tissue Res.* 25:205–207 (1978)]. Each osteoblast carries out a cycle of matrix synthesis after which it becomes either buried as an internal osteocyte or remains as a surface but inactive osteocyte or resting osteoblast. The cellular level of control focuses on the premise that new bone formation and regulation is the result of activating resting osteoblasts or the proliferation and subsequent differentiation of new osteoblasts. Once activation occurs, it is the rate at which each osteoblast produces bone matrix or the duration of bone matrix synthesis which is the regulatory mechanism of control. It is widely believed, but not yet proven, that osteoblasts have a direct role in the regulation of bone mineralization. The fact that newly formed bone matrix does not mineralize immediately indicates that the matrix must undergo some changes before mineralization can occur [Raisz and Kream, *N. Eng. J. Med.* 309:29–35 (1983)].

The molecular matrix level of understanding and investigation focuses upon the minerals and proteins comprising bone itself. The minerals in the bone matrix are calcium and phosphate which typically take the form of hydroxylapatite [Termine, J. D., *Clin. Orthop.* 85:207–241 (1972); Blumenthal et al., *Calcif. Tiss. Res.* 18:81–90 (1975)]. The primary protein of the bone matrix is collagen which is secreted as procollagen by osteoblasts and assembled extracellularly into fibrils stabilized by intramolecular and intermolecular cross-linkages. In addition to collagen, the bone matrix comprises other protein secretions of osteoblasts. These include sialoprotein [Herring, G. M., *Calcif. Tiss. Res.* 24:29–36 (1977)]; osteocalcin [Poser et al., *J. Biol. Chem.* 255:8685–8691 (1980)]; and osteonectin [Termine et al., *J. Biol. Chem.* 256:10403–10408 (1981)]. The role of these noncollagenous proteins in normal and pathological human bone remains an area of considerable research [Quelch et al., *Calcif. Tiss. Int.* 36:545–549 (1984)]. Bone matrix also contains several plasma proteins as component compositions. These include serum albumin and $\alpha_2$ HS-glycoprotein. Of all the compositions comprising the molecular matrix of bone, the presence of the $\alpha_2$ HS-glycoprotein in the bone matrix remains a continuing mystery.

$\alpha_2$ HS-glycoprotein was first isolated from normal human serum more than twenty-five years ago [Schmid and Burgi, *Biochim. Biophys. Acta* 47:440–453 (1961)]. This compound is a glycosylated, sulfate containing human serum protein consisting of two disulfide-linked polypeptide chains whose total molecular weight is approximately 50,000 daltons; the entirety of the amino acid sequences in each polypeptide chain has been established [Gejyo and Schmid, *Biochim. Biophys. Acta* 671:78–84 (1981); Gejyo et al., *J. Biol. Chem.* 258:496–497 (1983); Yoshioka et al., *J. Biol. Chem.* 261:1665–1676 (1986)]. The $\alpha_2$ HS-glycoprotein is a negative acute phase reactant which is synthesized in the liver and displays genetic polymorphism [Lebreton et al., *J. Clin. Invest.* 64:1118–1129 (1979); Triffitt et al., *Nature* 262:226–227 (1967); Anderson et al., *Proc. Natl. Acad. Sci.* 74:5421–5425 (1977)]. Normal human serum levels of $\alpha_2$ HS-glycoprotein are in the range of 600–660 micrograms per milliliter (hereinafter "µg/ml") of serum [Dickson et al., *Calcif. Tiss. Res.* 35:16–20 (1983)] with the highest concentrations being found in young adults. Curiously, the concentration of $\alpha_2$ HS-glycoprotein is reduced in humans afflicted with active Paget's disease [Ashton et al., *Clin. Sci.* 58:435–438 (1980)]; in persons having various solid tumors [Bradley et al., *Cancer* 40:2264–2272 (1977); Baskies et al., *Cancer* 45:3050–3060 (1980)]; and in individuals suffering from multiple myeloma [Crawford, S. M., *Br. J. Cancer* 49:813–815 (1984); Wiedermann et al., *Neoplasma* 25:189–196 (1978)]. This plasma protein is present in normal human cortical bone where it is concentrated approximately 140 fold with respect to other plasma proteins [Ashton et al., *Calcif. Tiss. Res.* 22:27–33 (1976); Triffitt et al., *Calcif. Tiss. Res.* 26:155–161 (1978); Quelch et al., *Calcif. Tiss. Int.* 36:545–549 (1984)]. Moreover, the concentration of $\alpha_2$ HS-glycoprotein varies as a function of age with the concentration in fetal bone being more than ten times greater than the concentration in adult bone [Wilson et al., *Calcif. Tiss. Res.* 22:(Suppl.):458 (1977); Dickson and Bagga, *Conn. Tiss. Res.* 14:77–85 (1985)]. It is generally believed that $\alpha_2$ HS-glycoprotein becomes concentrated in the bone matrix during mineralization due to its affinity for hydroxylapatite or calcium [Triffitt et al., *Nature* 262:226–227 (1967); Dickson et al., *Nature* 256:430–432 (1974)].

Despite this abundance of knowledge and data regarding $\alpha_2$ HS-glycoprotein, the true role and biological function of this protein, if any, is yet to be established. As part of its observed properties, $\alpha_2$ HS-glycoprotein is said to be an opsonin [Van Oss et al., *Immunol. Commun.* 3:329–335 (1974)]; to bind barium ions [Schmid and Burgi, *Biochim. Biophys. Acta* 47:440–453 (1961)]; to bind calcium ions [Ashton et al., *Calcif. Tiss. Res.* 22:27–33 (1976); Triffitt et al., *Nature* 262:226–227 (1976)]; to adhere to DNA [Lewis and Andre, *FEBS Lett.* 92:211–213 (1978)]; and to promote endocytosis by macrophages [Lewis and Andre, *Immunology* 39:317–322 (1980)]. Despite these reports, it is generally accepted in this scientific community that the biological function and true role of $\alpha_2$ HS-glycoprotein in bone formation and bone regulation remains unknown and unappreciated to date.

SUMMARY OF THE INVENTION

The present invention comprises a series of three related, but distinctly different, methodologies. The first is a method for inducing general bone apposition in-vivo; the second is a method for inducing localized bone apposition in-vivo at a preselected site; the third is a method for therapeutically treating pathological disorders of bone which are characterized by a deficiency or absence of calcium in the bone matrix. Each method comprises the step of administering sufficient $\alpha_2$ HS-glycoprotein to the subject generally or locally such that an effective concentration of $\alpha_2$ HS-glycoprotein is delivered to the serum or the localized site. For generalized skeletal treatment and for calcium deficient disorders, sufficient $\alpha_2$ HS-glycoprotein is administered such that not substantially less than 600 micrograms of $\alpha_2$ HS-glycoprotein per milliliter of serum is maintained. For localized site treatment, a therapeutic admixture comprising about 120–320 micrograms of $\alpha_2$ HS-glycoprotein per gram of filler material is administered to the local defect. While the present invention is intended primarily for use with humans, it is also applicable to animal subjects in a variety of veterinary situations and circumstances.

DETAILED DESCRIPTION OF THE FIGURES

Figure 1:
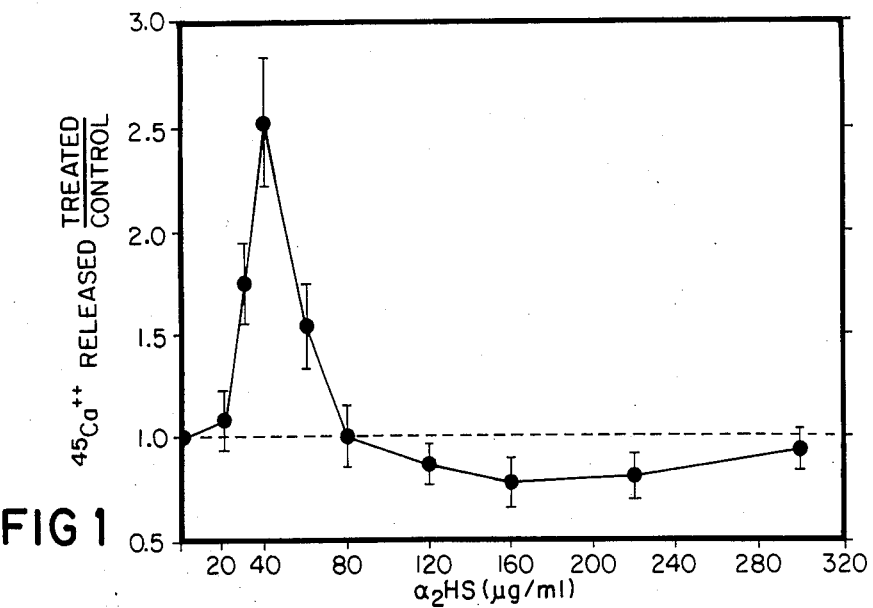
Figure 2:
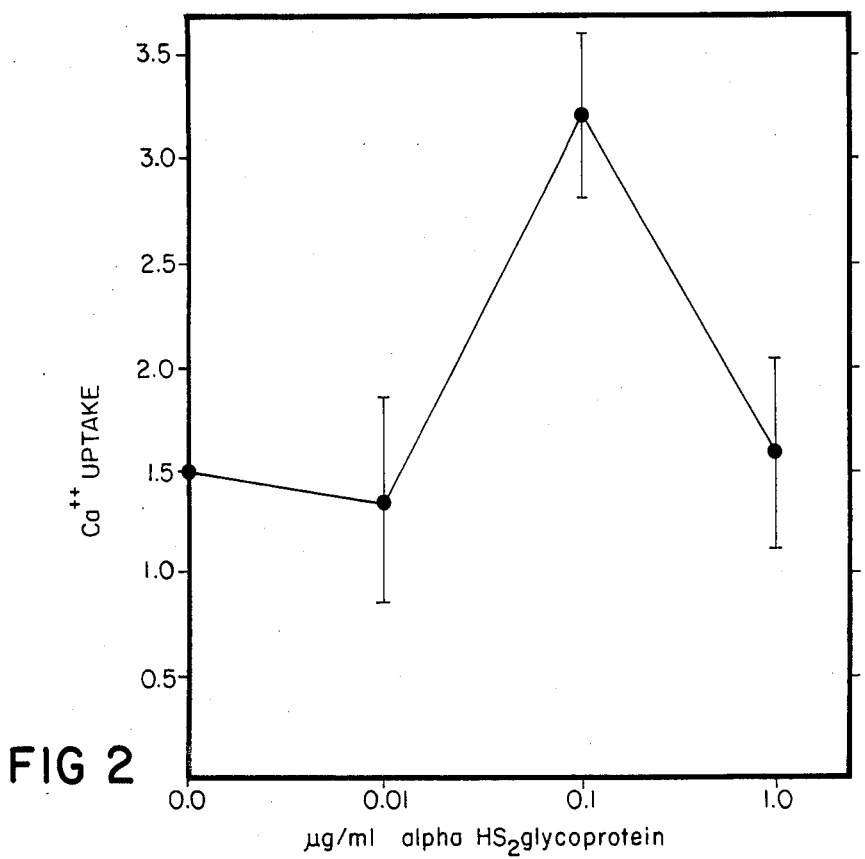

The present invention may be more easily and completely understood when taken in conjunction with the accompanying drawing, in which:

FIG. 1 is a graph illustrating the in-vitro biological activity of $\alpha_2$ HS-glycoprotein to effect bone apposition or bone resorption in mouse calvarial organ cultures as a function of its concentration; and FIG. 2 is a graph illustrating in-vitro uptake and release of calcium ion by human osteoblasts as a function of $\alpha_2$ HS-glycoprotein concentration.

DETAILED DESCRIPTION OF THE PREFERRED EMBODIMENTS

The present invention is a methodology for inducing the formation of new bone in-vivo generally or at localized sites within the skeleton of a subject. The formation of new bone or bone apposition is desirable in a variety of different conditions: osteoporesis; for the repair of bone injuries such as fractures or other similar wounds; in the remodeling of bone, particularly in dentistry for tooth and jaw alterations; in the restoring of lost bone at a site where there is no bone matrix; and as a therapeutic treatment for clinically and radiographically diagnosable disorders and diseases of bone which are characterized by a state of calcium deficiency in the subject.

The present invention utilizes and relies upon the unique finding and demonstration that the $\alpha_2$ HS-glycoprotein is biologically active and functional as a chemical regulator of both bone resorption and bone apposition. As will be empirically demonstrated hereinafter, when $\alpha_2$ HS-glycoprotein is present in the fluid environment surrounding existing bone in a concentration less than a minimal threshold level, generalized bone resorption occurs; conversely, when $\alpha_2$ HS-glycoprotein is present in the fluid environment surrounding existing bone at a concentration equal to or greater than a minimal threshold value, general bone apposition is initiated. The minimal threshold value correlates directly with those concentrations of $\alpha_2$ HS-glycoprotein considered normal and sub-normal in humans. Accordingly, so long as the $\alpha_2$ HS-glycoprotein concentration in a human subject remains at normal levels, typically 600–700 micrograms per milliliter of serum, normal bone apposition will occur. Alternatively, when the concentration of $\alpha_2$ HS-glycoprotein in the serum of the human subject is substantially less than about 600 $\mu$g/ml, a process of generalized bone resorption will be initiated. Whether or not the degree of bone resorption becomes sufficiently severe as to become a clinically diagnosable pathological disorder of the bone which is characterized by a deficiency of calcium within the bone matrix, will depend upon the age, general health, and bone condition of the individual. It will be understood however, that whether or not a clinically manifested pathology is present, some bone resorption, identifiable by an increasing loss of calcium ion from the bone matrix, will occur.

It will be appreciated, therefore, that the methodology comprising the subject matter as a whole of the present invention, regardless of specific application or use, comprises the step of administering an effective quantity of $\alpha_2$ HS-glycoprotein to the subject, the quantity varying with the nature and incidence of the disorder. For the treatment of bone disorders characterized by a deficiency or absence of calcium in the bone matrix and for treatment of generalized skeletal disorders, a sufficient concentration of $\alpha_2$ HS-glycoprotein is added to the serum of the subject such that the concentration of $\alpha_2$ HS-glycoprotein in the serum is maintained at a value not substantially less than 600 micrograms per milliliter of serum, and is preferably in the 600–700 $\mu$g/ml range. In certain instances, persons demonstrating $\alpha_2$ HS-glycoprotein concentrations as low as 100–200 $\mu$g/ml have been observed; such persons would then be administered concentrations of $\alpha_2$ HS-glycoprotein in sufficient quantities that the 400–500 $\mu$g/ml deficiency is alleviated. The resulting 600–700 $\mu$g/ml value of $\alpha_2$ HS-glycoprotein in the serum is deemed to be equally useful to promote new bone formation generally and to reverse the loss of calcium ions from the bone matrix of the subject in clinical cases of osteoporosis.

The administration of the glycoprotein can be made by any means that effects the concentration of the glycoprotein in the serum of the subject and maintains it in the desired range of about 600–700 μg/ml. Clearly, the quantity administered per individual will depend upon the age, general health, and weight of the recipient; the kind of concurrent treatment, if any; the presence or absence of an identifiable pathological disorder or disease in the bone; and the initial concentration of $\alpha_2$ HS-glycoprotein then present in the serum of the subject. It is expected also that the administration may be given in single dosage or multiple dosage regimen, the quantity of each dose varying with the needs of the individual and the therapeutic result to be obtained.

In addition, it is expected within this mode that the primary means of administration will be by parenteral injection. Accordingly, preparations of the glycoprotein will be made such that they exist in sterile form; are available in multiple or single dose formats; and are dispersed in a fluid carrier such as sterile physiological saline or 5% dextrose solutions commonly used with injectables. Other routes of administration such as oral or topical introduction may also be effective to achieve the requisite concentration of $\alpha_2$ HS-glycoprotein in the serum of the subject.

For the treatment of localized defects in bone, regardless of specific application or use, the method comprises the step of administering a sufficient quantity of $\alpha_2$ HS-glycoprotein to the localized boney defect such that a total concentration of $\alpha_2$ HS-glycoprotein is maintained at the specific site which is not substantially less than 120 micrograms per gram of solid matter. In this localized mode of treatment, abnormalities such as cysts, boney fracture sites, and places of peridontal disease related bone loss will receive a therapeutic admixture composed of $\alpha_2$ HS-glycoprotein and a filler material which is biologically compatible with the local defect, such as hydroxyapatite. The admixture will preferably contain about 200 micrograms of $\alpha_2$ HS-glycoprotein per gram of filler material; alternatively, a range from about 120–320 micrograms of $\alpha_2$ HS-glycoprotein per gram of filler material may be advantageously employed. In each instance, however, a total effective concentration is to be maintained which is not substantially less than about 200 micrograms per gram of solid matter.

In order to insure proper administration of the admixure, the local pathological defect preferably will be debrided surgically and the therapeutic admixture carried and placed in the local site by hand using aseptic procedures. The use of the filler material in combination with the appropriate quantity of $\alpha_2$ HS-glycoprotein aids in the long-term retention of the $\alpha_2$ HS-glycoprotein within the confines of the local area to be treated; acts to fill the cavitation spaces at the local site; and serves as a scaffolding for the ingrowth of induced new bone.

Procedures for isolating and purifying $\alpha_2$ HS-glycoprotein from Cohn fraction VI are conventionally known in the scientific community [Schmid and Burgi, *Biochim. Biophys. Acta* 47:440–453 (1961)] and are emminently suitable to obtain the glycoprotein in bulk quantities. An alternate procedure can be utilized to obtain $\alpha_2$ HS-glycoprotein from mixed pools of human serum drawn from males and females ages 22–41 respectively [Lamkin et al., *Cancer Res.* 46:4650–4655 (1986)]. The procedure, in brief, comprises: adding solid ammonium sulfate to the pooled human serum until a 50% saturated solution was achieved. The precipitate is suspended in water; dialyzed twice against 1 mM NaCl and once against distilled water; and lyophilized in the conventionally known manner. Subsequently, the ammonium sulfate precipitate is dissolved in 30 mM sodium acetate buffer, pH 5.0 and centrifuged. The supernatant form is applied to a DEAE-cellulose column which was previously equilibrated with 50 mM sodium acetate buffer, pH 5.0. After washing the column with this buffer, the proteins are eluted stepwise using 0.1 M sodium acetate buffer, pH 5.0.

The latter fraction from the DEAE-cellulose ion exchange column is then dissolved in 10 mM potassium phosphate buffer, pH 7.2, containing 0.15 M NaCl (40 mg/ml); centrifuged at 6000 x gravity for 30 minutes; and filtered. The protein preparation is then applied to a preparative TSK 3000 SW column (2.1×30 cm) in 1.5 ml aliquots. A liquid chromatography system equipped with an ultraviolet-visible spectrophotometric detector set to 280 nanometers is used to monitor the course of fractionation during high performance liquid chromatography.

The protein fraction isolated from the preceding high performance, size exclusion chromatography is dissolved in 10 mM potassium phosphate buffer, pH 6.8 at a concentration of 30 mg/ml; centrifuged at 3000 x gravity for 10 minutes; and applied to a hydroxylapatite column (2.0×20 cm) previously equilibrated with the same buffer. After washing the column with the buffer the adsorbed proteins are eluted with successive rinses of 5.0 mM, 100 mM, and 500 mM potassium phosphate buffer, pH 6.8. Finally, the protein fraction eluted from hydroxylapatite is subjected to high performance anion exchange chromatography. The protein fraction is dissolved in 10 mM potassium phosphate buffer, pH 7.2 at a concentration of 30 mg/ml; centrifuged at 5000 x gravity for 30 minutes and 0.1 ml aliquots applied to a TSK DEAE 5 PW column. Elution is accomplished using 0.0–0.5 M NaCl gradient in 10 mM sodium phosphate buffer, pH 7.2 using the high performance liquid chromatography apparatus. The purified protein is evaluated using commercially prepared rabbit anti-$\alpha_2$ HS-glycoprotein antiserum purchased from Calbiochem-Behring Corporation (La Jolla, Calif.). The purified protein can be evaluated chemically for purity by N-terminal sequencing and/or electrophoresis in the conventionally known manner.

It will be recognized that the isolation and purification conditions used to obtain $\alpha_2$ HS-glycoprotein are relatively mild and result in a monodispersed protein preparation able to demonstrate specific biological activity. It will be appreciated also that the true chemical composition of human $\alpha_2$ HS-glycoprotein as a molecule consisting of two distinct polypeptide chains and a nominal molecular weight of 52,000 daltons is known in this art [Gejyo and Schmid, *Biochim Biophys. Acta* 671:78–84 (1981); Gejyo et al., *J. Biol. Chem.* 258:4966–4971 (1983); Yoshioka et al., *J. Biol. Chem.* 261:1665–1676 (1986)]. For this reason, the detailed description of the amino acid sequence comprising the polypeptide chain or the general chemical characteristics need not and will not be described herein.

In order to properly illustrate the present methodology and to demonstrate the unique biological functions and characteristics of $\alpha_2$ HS-glycoprotein with respect to bone apposition and the calcium content of bone matrix, the following experiments are provided. It will be expressly understood however that these experiments do not limit the scope of and do not restrict the use of the $\alpha_2$ HS-glycoprotein to the described empirical circumstances, applications, or uses.

Experiment 1

The biological activity of the $\alpha_2$ HS-glycoprotein isolated and purified in the manner described above, was assessed by measuring the release of $^{45}Ca$ ions from explants of newborn mouse calvaria maintained in organ culture as previously described in Nimberg et al., J. Biol. Chem. 257:2477–2482 (1982). In brief, litters of one-day old CD-1 mice receive subcutaneous injections of 10 $\mu Ci$ of $^{45}CaCl_2$. Four days later, the mice are sacrificed and their calvaria excised, trimmed of remnants of occipital bone and cartilage, and divided into paired halves. Subsequently, each half-calvaria is positioned onto a stainless steel mesh grid; placed into a petri dish containing 2.5 ml $BGJ_b$ medium; and precultured for 72 hours at 37 C in a humidified air atmosphere containing 5% $CO_2$. One half-calvarium is then transferred to $BGJ_b$ media containing a predetermined concentration of $\alpha_2$ HS-glycoprotein while the other half-calvaria is transferred to fresh $BGJ_b$ medium alone and serves as a control. Both half-calvaria in their respective media are then incubated as before for 72 hours at 37° C. The release of $^{45}Ca$ into the medium from each half-calvarium is then measured by liquid scintillation spectrometry in the conventionally known manner. At least four pairs of calvaria were employed per experiment. The results are shown by FIG. 1.

Biological activity is expressed as the mean of the ratio of $^{45}Ca$ release into the medium from the half-calvarium containing $\alpha_2$ HS-glycoprotein in comparison to the $^{45}Ca$ release in the control medium from the samples. An overall increase in $^{45}Ca$ ion release into the medium is indicative of bone resorbing activity. One unit of bone resorbing activity is defined as a 50% increase in the release of $^{45}Ca$ ion from the treated calvarium over the untreated, control calvarium. It should be noted that the treated/control (hereinafter "T/C") ratios of the media from paired half-calvaria exposed to either inactive preparations or no protein are very close to unity. In comparison, half-calvaria exposed to active bone resorbing preparations demonstrate the release of more than twice the $^{45}Ca$ ion concentration into the surrounding medium as the corresponding controls. As a guideline, this assay system demonstrates that parathyroid hormone (hereinafter "PTH") in the form of a synthetic bovine parathyroid fragment containing amino-terminal residues 1-34 (Bachem Inc, Torrence, Calif.) demonstrates one bone resorbing unit of activity when 0.1 $\mu g/ml$ of PTH is employed in this assay.

Conversely, one unit of bone apposition activity is defined as a 50% decrease in the release of $^{45}Ca$ ions from the treated half-calvarium over the comparable control. The influx of $^{45}Ca$ ions into the half-calvarium is deemed to be evidence of bone apposition and mineralization of the bone matrix.

The empirical data presented by FIG. 1 demonstrates that the plasma derived $\alpha_2$ HS-glycoprotein is capable of modulating $^{45}Ca$ ion flux from bone. Clearly, concentrations of $\alpha_2$ HS-glycoprotein up to 60 H $\mu g/ml$ causes bone resorption from calvarial explants. Note that a maximum effect is observed at the 40 $\mu g/ml$ concentration at which a 250% increase in $^{45}Ca$ ion release (T/C ratio =2.5 ±0.34; $P<0.01$) is obtained. In comparison, concentration of $\alpha_2$ HS-glycoprotein above 80 $\mu g/ml$ reduce calcium ion mobilization and induce an influx of $^{45}Ca$ ions into the bone matrix - a demonstration of new bone apposition. A maximum effect of calcium influx is observed at the 160 $\mu g/ml$ concentration (T/C ratio =0.77±0.11; $P<0..05$). With further increases in the concentration of $\alpha_2$ HS-glycoprotein in the medium, a gradual reversal of this calcium influx occurs; the highest concentration tested, 300 $\mu g/ml$, demonstrates little or no effect on calcium influx and comparably little bone apposition as a result.

It should be noted that the efflux and influx of $^{45}Ca$ ions from bone explants in this assay system are specific effects of $\alpha_2$ HS-glycoprotein concentrations exclusively. This is clearly demonstrated by the failure of other protein preparations such as human serum albumin, human serum $\alpha_2$-acid glycoprotein, ceruloplasmin, and transferin to effect any change whatsoever in $^{45}Ca$ ion release when tested at concentrations equal to or greater than those utilized for $\alpha_2$ HS-glycoprotein. In addition, it should be noted that when this experimental series was repeated using reaction mixtures of $\alpha_2$ HS-glycoprotein in combination with specific anti-($\alpha_2$ HS-glycoprotein) IgG, the biological activity demonstrated by the data of FIG. 1 is absent. Clearly therefore, the incubation of this glycoprotein with specific antibody abolishes its biological activity in all respects. This experimental result also demonstrates the influx or efflux of $^{45}Ca$ ions and the ability to initiate bone apposition to be a specific result and effect of $\alpha_2$ HS-glycoprotein at concentrations above 80 $\mu g/ml$.

With regard to the concentrations of $\alpha_2$ HS-glycoprotein employed in this experimental series, it is deemed that the empirically tested 160 $\mu g/ml$ concentration providing the maximal influx of calcium ions and new bone apposition is comparable to the normal levels of this glycoprotein in human serum or plasma - that is, the concentration ranging from 600–700 $\mu g$ per ml of serum. While it is noted that concentrations above the empirically tested 80 $\mu g/ml$ concentration begin to demonstrate influx of calcium, the maximum effect is observed at the 160 $\mu g/ml$ concentration. Accordingly, with living human and animal subjects, maintaining less than the 600 $\mu g/ml$ concentration of $\alpha_2$ HS-glycoprotein in the subject is not considered to be truly beneficial or therapeutic in nature. For this reason, therefore, it is desirable that a sufficient quantity of $\alpha_2$ HS-glycoprotein be administered to the subject such that not less than a 600 $\mu g/ml$ concentration is achieved in the serum of the subject.

Experimental Series 2

This experimental series demonstrates the effect of increasing concentrations of $\alpha_2$ HS-glycoprotein upon the calcium ion levels in the blood when administered systemically to intact mice. 7-9 week old male mice of the pure bred Swiss Albino strain were used in treatment groups of ten mice each. Each mouse in a group of ten weighed between 28–32 grams and was maintained on a rodent chow diet.

Each of the ten mice in a treatment group received 7 identical subsutaneous injections in the back of the neck over a 48 hour time period of only one of the following: Bovine parathyroid extract (Eli Lilly Co.), 2 units per injection; $\alpha_2$ HS-glycoprotein at 0.05 mg per injection; $\alpha_2$ HS-glycoprotein at 0.50 mg per injection; $\alpha_2$ HS-glycoprotein at 1.00 mg per injection; and human albumin in saline (control) at 1.00 mg per injection. Ether was used for anesthesia of each mouse during injection and during subsequent blood withdrawal.

Four hours after the final injection was given, the blood from each mouse in a treatment group was drawn using heparinized syringes. None of the mice in any treatment group were parathyroidectomized. The individual blood samples were randomized for each treatment group and the plasma calcium content of the randomized blood determined by automatic fluorometric titration using a calcium analyzer (Model 940, Corning Corp.). The results are proved by Table I below. The results reveal a measurable reduction of calcium ions in the randomized blood drawn from each treatment group receiving $\alpha_2$ HS-glycoprotein.

TABLE 1

| MATERIAL | TOTAL SERUM CALCIUM (mg/dl) |
|---|---|
| Human Albumin in Saline/Control | 9.28 ± 0.28/treatment group of 10 |
| Parathroid Hormone, 2 units | 10.03 ± 0.33/treatment group of 10 |
| $\alpha_2$ HS-glycoprotein @ 0.05 mg | 8.93 ± 0.33/treatment group of 10 |
| $\alpha_2$ HS-glycoprotein @ 0.50 mg | 9.17 ± 0.32/treatment group of 10 |
| $\alpha_2$ HS-glycoprotein @ 1.00 mg | 8.99 ± 0.33/treatment group of 10 |

Experimental Series 3

To further demonstrate the biological activity of $\alpha_2$ HS-glycoprotein, another series of experiments were undertaken to demonstrate the uptake of calcium ions by human osteoblasts. The experimental protocol was as follows. A human osteosarcoma cell line (SaOS-2), which consists of enriched normal human osteoblasts, was grown and cultured as a monolayer of cells in the conventionally known manner. These cultured cells were harvested and suspended at a concentration of $1.5 \times 10^6$ cells per milliliter in modified HEPES buffer, pH 7.4 (Sigma Chemical Co., St. Louis, MO). To 1.0 ml aliquots of this cell suspension were added from 0.01–1.0 µg of $\alpha_2$ HS-glycoprotein. Controls consisted of cell aliquots suspended in modified HEPES buffer alone. Each of the test and control cell suspensions were first preincubated for 15 minutes at 37° C. in a shaker bath. Subsequently, 2 µCi/ml of $^{45}Ca$ ions in the form of $^{45}CaCl$ was added to each aliquot and the reaction mixtures incubated for 5 additional minutes at 37° C. At the end of the 5 minute reaction period, the calcium uptake by the cells was terminated via the addition of 5.0 ml cold HEPES buffer to each aliquot. The diluted cell suspensions were then immediately individually filtered through a 0.45 µm filter (DAWP filter, Millipore Corporation). The particulate matter on the filter surface was then rinsed with 5.0 ml of ice cold HEPES buffer. Each filter paper was then dried and immersed in 10.0 ml of scintillation liquid. The radioactivity was then measured by liquid scintillation spectroscopy in the conventionally known manner. The results are illustrated by FIG. 2.

FIG. 2 reveals that increasing concentrations of $\alpha_2$ HS-glycoprotein cause corresponding increases in calcium uptake by human osteoblasts in-vitro. The threshold level of significant calcium uptake increase begins at a concentration of 0.01 µg/ml of the glycoprotein. As a guideline, in this assay system 0.2 µg of PTH/ml (bovine PTH, amino-terminal fragment residues 1–34; Sigma Chemical Co., St. Louis, MO) is known to produce calcium uptake by human osteoblasts in-vitro; however, the calcium uptake caused by 0.2 µg/ml of PTH is equivalent to that produced by 0.1 µg/ml of $\alpha_2$ HS-glycoprotein. The biological activity of the ahd 2 HS-glycoprotein is thus far more potent than that demonstrated for PTH.

The present invention is not to be restricted in form nor limited in scope except by the claims appended hereto.

What we claim is:

1. A method for inducing general bone apposition invivo comprising the step of:
    administering sufficient $\alpha_2$ HS-glycoprotein to a subject such that the concentration of said $\alpha_2$ HS-glycoprotein in the serum of the subject is maintained at not substantially less than about 600 micrograms per milliliter of serum.

2. A method for therapeutically treating pathological disorders of bone characterized by a deficiency of calcium ions in the bone matrix of the subject, said method comprising the step of:
    administering sufficient $\alpha_2$ HS-glycoprotein to a subject such that the concentration of $\alpha_2$ HS-glycoprotein in the serum of the subject is maintained at not substantially less than about 600 micrograms per milliliter of serum.

3. The method as recited in claim 1 or 2 wherein said administration of $\alpha_2$ HS-glycoprotein to the subject maintains a concentration of $\alpha_2$ HS-glycoprotein in the range of about 600–700 micrograms per milliliter of serum.

4. A method for inducing localized bone apposition invivo at a predetermined site comprising the step of:
    administering a therapeutic admixture to the localized site, said admixture comprising a filler material and a concentration of $\alpha_2$ HS-glycoprotein ranging from 120–320 micrograms per gram of filler material.

5. The method as recited in claim 4 wherein said filler material comprises hydroxyapatite.

* * * * *